United States Patent [19]

Cecco et al.

[11] Patent Number: 4,855,676
[45] Date of Patent: * Aug. 8, 1989

[54] FERROMAGNETIC EDDY CURRENT PROBE HAVING TRANSMIT AND RECEIVE COIL ASSEMBLIES

[75] Inventors: Valentino S. Cecco; Jon R. Carter, both of Deep River, Ontario, Canada

[73] Assignee: Atomic Energy of Canada Limited, Ottawa, Canada

[*] Notice: The portion of the term of this patent subsequent to Feb. 28, 2006 has been disclaimed.

[21] Appl. No.: 46,549

[22] Filed: May 6, 1987

[51] Int. Cl.⁴ ..................... G01N 27/90; G01R 33/12
[52] U.S. Cl. .............................. 324/220; 324/225; 324/232; 324/242
[58] Field of Search .............. 324/219, 220, 221, 239, 324/240, 241, 242, 232, 225

[56] References Cited

U.S. PATENT DOCUMENTS

| 2,124,579 | 7/1938 | Knerr et al. | 324/242 |
| 3,952,315 | 4/1976 | Cecco | 324/220 |
| 4,808,924 | 2/1989 | Cecco et al. | 324/220 |
| 4,808,927 | 2/1989 | Cecco et al. | 324/220 |

OTHER PUBLICATIONS

Cecco, "Design . . . of a High Saturation . . . Eddy Current Probe . . ." Materials Evaluation, vol. 37, No. 13, 1979, pp. 51–58.

Primary Examiner—Reinhard J. Eisenzopf
Assistant Examiner—Walter E. Snow
Attorney, Agent, or Firm—Yoshiharu Toyooka

[57] ABSTRACT

An eddy current probe capable of detecting localized defects in a ferromagnetic tube is disclosed. The probe employs a transmit coil assembly and a receive coil assembly. Means for magnetically saturating the tube near the transmit and receive coil assemblies is also disclosed.

6 Claims, 3 Drawing Sheets

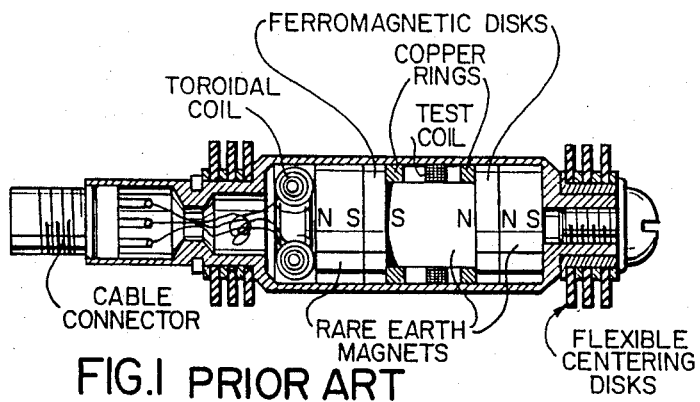
FIG.1 PRIOR ART
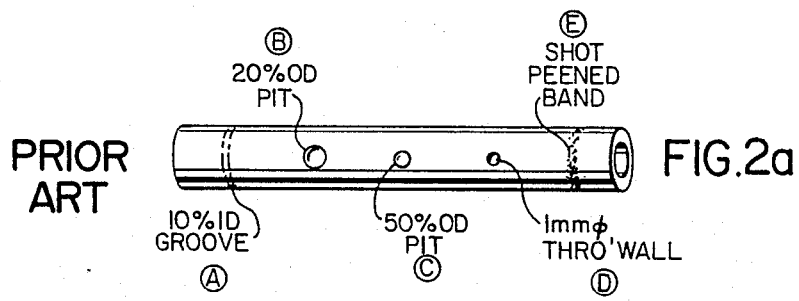
PRIOR ART FIG.2a
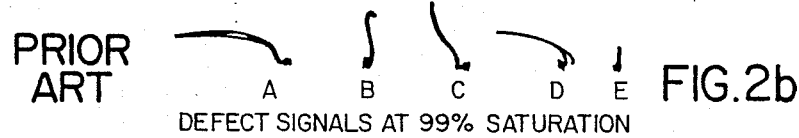
PRIOR ART FIG.2b
DEFECT SIGNALS AT 99% SATURATION
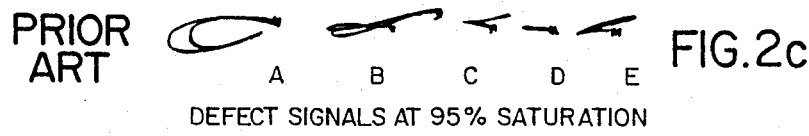
PRIOR ART FIG.2c
DEFECT SIGNALS AT 95% SATURATION

FERROMAGNETIC EDDY CURRENT PROBE HAVING TRANSMIT AND RECEIVE COIL ASSEMBLIES

This invention relates to an apparatus and a method for detecting localized flaws in a tube of a ferromagnetic material. More specifically, the invention relates to a ferromagnetic tube flaw detection technique which utilizes magnetic saturation and a transmitreceive eddy current probe for measurement.

BACKGROUND OF THE INVENTION

In the past, bodies of ferromagnetic material have been inspected by a method such as the leakage flux method as taught, for example, in U.S. Pat. Nos. 3,091,733, May 28, 1963 Fearer et al and 4,602,212, July 22, 1986, Hiroshima et al. In this method, the metal is magnetized in a direction parallel to its surface. At defects or where regions of the metal body are thinner, some magnetic flux passes into the air and may be detected by sensor, thus giving an indication of the presence of faults.

U.S. Pat. No. 4,107,605, Aug. 15, 1978 Hudgell discloses an eddy current technique for testing of pipelines of ferrogmagnetic material. The probe includes spiral sensing coils placed with their axes normal to the surface of the pipeline wall and connected on four legs of an AC bridge, thus compensating for lift-off, Biasing electromagnetic fields permit distinguishing internal from external defects in weakly ferromagnetic tubes by comparing outputs from systems with and without biasing fields.

In U.S. Pat. Nos. 2,992,390, July 11, 1961 Dewitte and 3,940,689 Feb. 24, 1976 Johnson, Jr., special ways of generating magnetic fields are taught in connection with the eddy current testing in that DeWitte uses uniquely designed core and Johnson, Jr. employs a solenoid wound about a core of a substantial length. U.S. Pat. No. 4,292,589 Sept. 29, 1981 Bonner on the other hand teaches the use of unique coil arrangements for a differential receiver of a remote-field eddy current probe. However, his arrangement requires long probes and low test frequency, thus limiting inspection speed. U.S. Pat. Nos. 3,952,315 Apr. 20, 1976 Cecco and 2,964,699 Dec. 6, 1960 Perriam describe probes for use of testing weakly ferromagnetic tubes. They use impedance type sensing circuit but are not sensitive to circumferential cracks nor are they circumferentially compensating either.

All the prior art instruments suffer from various shortcomings such as high cost, requirement of specially designed instrumentation, bulky electromagnetizers for high magnetic saturation, insensitivities for certain kinds of defects, no defect sensitivity close to weld joints etc.

OBJECTS OF THE PRESENT INVENTION

It is herefore an object of the present invention to provide an eddy current probe for inspecting ferromagnetic tubes which is small and less expensive to manufacture and to use.

It is another object of the present invention to provide an eddy current probe having specially designed transmit and receive coils which permit circumferential compensation while retaining high sensitivity to localized defects.

SUMMARY OF THE INVENTION

Briefly stated, in accordance with the present invention, an eddy current probe for detecting localized flaws in a tube made of a ferromagnetic material includes a transmit coil assembly and at least one receive coil assembly, all positioned in a probe casing along its axis at a predetermined distance from each other. The probe further has magnet means for magnetizing the tube to magnetically saturate the tube near the transmit coil assembly and the receive coil assembly. The magnet means comprises a plurality of permanent magnets axially arranged in series in the probe housing, the polarity of one magnet being opposite to that of the adjacent magnet. One or more of the permanent magnets have a solenoid wound thereabout to be energized by dc.

BRIEF DESCRIPTION OF THE DRAWINGS

In a more complete understanding of the present invention and for further objects and advantages thereof, references may be made to the following description taken in conjunction with the accompanying drawings in which:

FIG. 1 is a schematic view of a prior art eddy current probe;

FIG. 2(a), 2(b) and 2(c) show a ferromagnetic stainless steel test tube and signals obtained by the probe shown in FIG. 1;

DETAILED DESCRIPTION OF THE PREFERRED EMBODIMENTS

Figure 3:
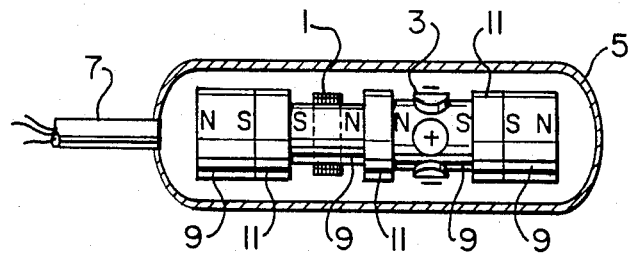
FIG. 3 is a schematic view of an eddy current probe of the present invention according to one embodiment.

Conventional eddy current testing detects changes in eddy current induced in an object under test. The eddy current is indirectly measured by a probe coil located near the surface of the object which monitors the magnetic flux created by the eddy current. However, when an eddy current probe is used for ferromagnetic tube inspection, the magnetic permeability of the ferromagnetic material affects the probe coils inductance as well as depth of eddy current penetration into the material. The magnetic permeabilitiy strongly depends on factors such as:

thermal processing history;
mechanical processing history;
chemical composition;
internal streses; and
temperature (if close to curie temperature).

The large variations in permeability make conventional eddy current testing for defects in magnetic materials very difficult.

The best solution to eddy current testing of a magnetic material for defects is to bring it to a condition where $\mu_r=1.0$. Relative incremental or recoil permeability, $\mu_r$, is defined as $\mu_r=\Delta B/\Delta H$ where $\Delta B$ is the change in flux density which accompanies a change in magnetizing force, $\Delta H$ created for example by an eddy current coils' alternating current.

A few slightly magnetic materials can be heated above their curie temperature to make them nonmagnetic. Monel (trademark) 400 heated to between 50° and 70° C. has been tested in this manner. Most materials, however, have too high a curie temperature to be tested by this approach. The only other way to decrease $\mu_r$ to unity is by magnetic saturation.

FIG. 1 shows a probe known in the art as the saturation probe which incorporates a permanent magnet configuration designed to maximize the saturation field over the test coil. The probe shown in the figure is described in Materials Evaluation Journal, Vol. 37, No. 13, 1979, pp. 51-58, "Design and specifications of a high saturation absolute eddy current probe with internal reference" by Cecco.

The importance of achieving maximum saturation is illustrated in FIG. 2(a), 2(b), and 2(c) which shows results from Type 439 stainless steel heat exchanger tube. A 15.9 mm OD by 1.2 mm thick tube with internal and external calibration defects and a shot peened area was used to compare the performance of various saturation probes. As shown in FIG. 2(a), the external defects ranged from 20 to 100% deep. FIG. 2(b) shows the signals obtained with a probe capable of 99% saturation and FIG. 2(c) signals with 95% saturation. The relative magnetic permeability ($\mu_r$) at 99% saturation is approximately 1.15 and at 95% saturation it is 1.9. At 99% saturation the eddy current signals from the external calibration holes display the characteristic phase rotation with depth, that one expects for nonmagnetic materials. In contrast, with only 95% saturation the signals are distorted and indistinguishable from "change in magnetic permeability" signals. From similar tests on other ferromagnetic tubes it has been found that at least 98% saturation is needed ($\mu_r \leq 1.3$) for reliable test results. This requires detailed optimization of the saturation magnet design for each ferromagnetic tube material. However, even the most optimized saturation probe cannot completely saturate some tubes especially carbon steel tubes or pipes.

Contrary to the prior belief, the inventors have discovered that when an eddy current probe having a transmit coil assembly and a receive coil assembly is used, only partial magnetic saturation, (e.g. of less than 50%) would suffice for good sensitivity in this and thick tubes of weakly or strongly magnetic material.

According to the present invention, the transmit coil generates a magnetic field and eddy currents that decrease rapidly with radial and axial distance. The magnetic field is much weaker but uniform axially and radially at a few coil diameters away from the transmit coil. In this periphery region the best signal-to-noise is obtained. Partial saturation is sufficient to decrease the magnetic permeability variations and allow the magnetic field to reach the tubes external defects.

Referring to FIG. 3 one of the preferred embodiments is illustrated to have a transmit coil assembly 1 and a receive coil assembly 3. The coil assemblies are housed in a probe casing 5 of a non-ferromagnetic material the probe casing housing an axis which substantially coincides with the central axis of a tube under inspection when the probe is located inside the tube. And an electrical connection is made at 7. Four permanent magnets 9 are arranged with their polarities as shown, that is, two adjacent ones being oppositely polarized. All the polarities of the magnets can be reversed with the same results. The transmit coil assembly is of a bobbin coil type in this embodiment and is positioned over the second magnet. The receive coil assembly 3 comprises a set of four pancake coils and is positioned over the third magnet. Magnetic field keeper disks 11 of a high $\mu_r$ material such as permendur (Trade Name) are placed between the permanent magnets 9. Four pancake coils of he receive coil assembly 3 are arranged 90° circumferentially apart from each other and oppositely polarized as shown for circumferential compensation. The distance along the axis of the casing between the transmit coil assembly and the receive coil assembly is set in this embodiment as being about twice the diameter of the bobbin coil which is roughly same as the diameter of the tube under test. While a bobbin coil and four pancake coils are illustrated in the figure; other coil configurations such as a plurality of pancake coils in a transmit coil assembly and more than four pancake coils in a receive coil assembly. The present applicant's co-pending applications Ser. No. 16,752 filed on Feb. 19, 1987, now U.S. Pat. No. 4,808,924 issued Feb. 28, 1989, "Circumferentially Compensating Eddy Current Probe with Alternately Polarized Transmit Coils and Receive Coils" and No. 16,748 filed on Feb. 19, 1987, now U.S. Pat. No. 4,808,927 issued Feb. 28, 1989, "Circumferentially Compensating Eddy Current Probe" describe various possible circumferentially compensating coil configurations.

Figure 4:
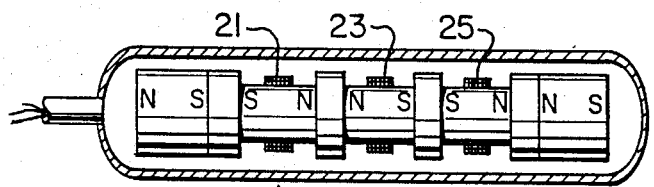
FIG. 4 is a schematic view of an eddy current probe of the present invention according to another embodiment.

Referring to FIG. 4, another embodiment is shown in which five permanent magnets are arranged in the same fashion as in FIG. 3. The bobbin transmit coil 21 is over the second magnet and two bobbin receive coils are located over the third and the fourth magnets. The axial distances of the receive coils from the common transmit coil are about D and 2D as shown in the figure, D being the diameter of the tube under test. Each receive coil 23, 25 is monitored separately. The receive coil 23 is sensitive to internal tube defects and the receive coil 25 to internal as well as external defects.

Figure 5:
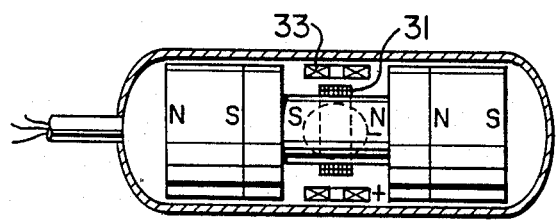
FIG. 5 is a schematic view of an eddy current probe of the present invention according to still another embodiment.

FIG. 5 shows a different embodiment which uses three permanent magnets. The transmit coil 31 is of a bobbin type and the pancake receive coils are four in number arranged 90° circumferentially apart from each other. The axial distance between the transmit and receive coils is zero.

Figure 6:
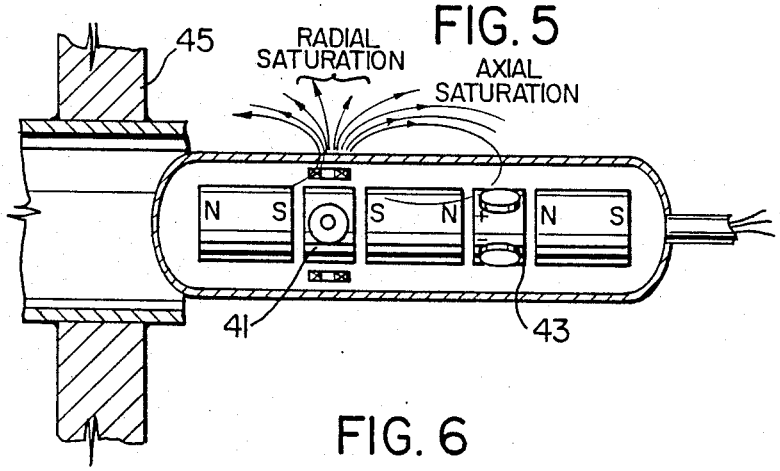
FIG. 6 is a schematic view of an eddy current probe of the present invention according to still another embodiment showing radial saturation.

While all the embodiments described so far utilize axial magnetic saturation along the tube under test, for some applications, such as detection of defects under ferromagnetic support plates, radial saturation is preferred. FIG. 6 shows one of such configurations for radial saturation. In the figure, three permanent magnets are arranged axially with magnetic field keeper disks 41 and 43 between them. Instead of over the permanent magnets as in the previous embodiments, four transmit coils and four receive coils are located over respective keeper disks 41 and 43. A typical tube support plate 45 is also shown.

Other coil configurations, e.g. 2 transmit coils and 2 receive coils over each keeper disk or a bobbin transmit coil and four receive coils over either separate keeper disks or over a same disk, are also possible.

In these embodiments, radial saturation increases slightly in the tube under support plates, as can be seen in the figure, whereas axial saturation drastically decreases, rendering inspection impossible.

Figure 7A:
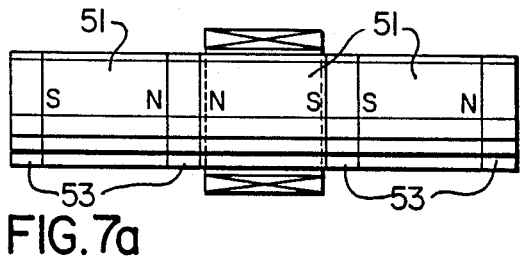
FIG. 7(a), 7(b), 7(c) and 7(d) illustrate various magnetic saturation configurations according to the present invention.
Figure 7B:
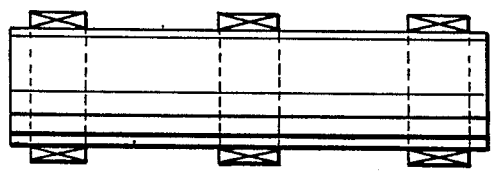
Figure 7C:
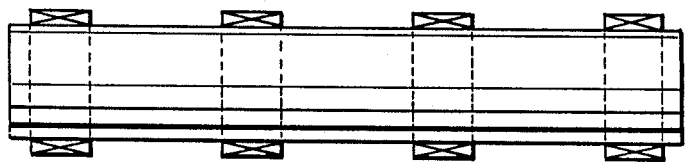
Figure 7D:
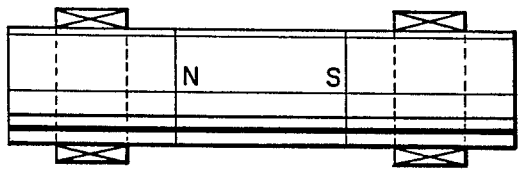

FIGS. 7(a), 7(b), 7(c) and 7(d) illustrate schematically other magnetic configurations in which the permanent magnets are completely replaced or are partially supplemented by dc magnets (dc powered electromagnets). In FIG. 7(a), an electromagnetic 51 is positioned over the middle permanent magnet. The energization of the electromagnetic facilitate finer controlling of the magnetic saturation. Since the resultant saturation flux density is a function of tube thickness, controlling the DC saturation allows tubes of various thickness to be inspected with the same probe at the optimized saturation condition. A high $\mu_r$ material 53 is also provided. In FIGS. 7(b), 7(c) and 7(d), electromagnets are provided on a high $\mu_r$ material such as permendur (Trade Name).

We claim:

1. A circumferentially compensating eddy current probe for detecting localized flaws in a tube made of a ferromagnetic material, comprising:
   a probe casing made of a non-ferromagnetic material and having an axis,
   a transmit coil assembly housed in the said probe casing,
   at least one receive coil assembly housed in the said probe casing at a predetermined distance from the said trasnmit coil assembly along the said axis,
   each of the said receive coil assembly having an even number of identical pancake coils located circumferentially and symmetrically in the said probe housing,
   alternate pancake coils in each receive coil assembly being electromagnetically polarized in opposite directions, and
   magnet means for magnetically saturating the tube, at least partially, only areas near the said transmit coil assembly and the said receive coil assembly.

2. The circumferentially compensating eddy current probe according to claim 1 wherein:
   the said receive coil assembly is one in number,
   the said magnet means comprises three magnets axially arranged in series in the probe casing, the polarity of one magnet being opposite to that of the adjacent magnet, and
   the said predetermined distance is zero, thus both the transmit and receive coil assemblies being located circumferentially over the middle magnet.

3. The circumferentially compensating eddy current probe according to claim 1 wherein:
   the said transmit coil assembly has an even number of identical pancake coils,
   the said receive coil assembly is one in number,
   the said magnet means comprises three magnets axially arranged in series in the probe casing, the polarity of one magnet being opposite to that of the adjacent magnet,
   ferromagnetic disk means are provided between and at the ends of the magnets, and
   the transmit and receive coil assemblies are each located circumferentially over each of the said disk means between the magnets where radial magnetic saturation is effected.

4. The circumferentially compensating eddy current probe according to claim 2 wherein each of the said three magnets is a permanent magnet.

5. The circumferentially compensating eddy current probe according to claim 3 wherein each of the said three magnets is a permanent magnet.

6. The circumferentially compensating eddy current probe according to claim 1 wherein:
   the said magnet means comprises four or more magnets, all axially arranged in series in the probe casing, the polarity of one magnet being opposite to that of the adjacent magnet, and
   the transmit coil assembly and at least one receive coil assembly are located on different magnets spaced apart from each other by a predetermined distance.

* * * * *